United States Patent [19]
Sisti et al.

[11] Patent Number: 5,750,737
[45] Date of Patent: May 12, 1998

[54] METHOD FOR PACLITAXEL SYNTHESIS

[76] Inventors: Nicholas J. Sisti, 450 Forest Ave., Apt. S204, Jeffersonville, Pa. 19401; Charles S. Swindell, 613 Schiller Ave., Merion, Pa. 19066

[21] Appl. No.: 719,488

[22] Filed: Sep. 25, 1996

[51] Int. Cl.$^6$ .................................................. C07D 305/14
[52] U.S. Cl. .......................................... 549/510; 549/511
[58] Field of Search ................................... 549/510, 511

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |
| 4,960,790 | 10/1990 | Stella et al. | 514/449 |
| 5,015,744 | 5/1991 | Holton | 549/510 |
| 5,136,060 | 8/1992 | Holton | 549/510 |

FOREIGN PATENT DOCUMENTS

| | | |
|---|---|---|
| 0400971 | 12/1990 | European Pat. Off. |
| 0528729A1 | 2/1993 | European Pat. Off. |
| 2687150 | 8/1993 | France |
| WO91/13066 | 9/1991 | WIPO |

OTHER PUBLICATIONS

"Biologically Active Taxol Analogues with Deleted A-Ring Side Chain Substitutents and Variable C-2' Configurations", Swindell et al, *Journal of Medicinal Chemistry*, 1991, vol. 34, No. 3 pp. 1176–1184.

"New Efficient Approaches to the Semisynthesis of Taxol and its C-13 Side Chain Analogs by Means of B–Lactam Synthon Method", Ojima et al, *Tetrahedron*, vol. 48, No. 34, pp. 6985–7012, 1992.

"Improved Protection and Esterification of a Precursor of the Taxotere and Taxol Side Chains", Commercon et al, *Tetrahedron Letters*, vol. 33, No. 36, pp. 5185–5188, 1992.

"Highly Sterocontrolled and Efficient Preparation of the Protected, Esterification–Ready Docetaxel (Taxotere) Side Chain", Kanazawa et al, *J. Org. Chem*, vol. 59, No. 6, pp. 1238–1240, 1994.

"Novel Biologically Active Taxol Analogues:Baccatin III 13–(N–(p–Chlorobenzoyl)–(2'R, 3'S)–3'–phenylisoserineate) and Baccatin III 13–(N–Benzoyl–(2'R, 3'S)–3'–(p–chlorophenyl)isoserinate)", Georg et al., *Bioorganic & Medicinal Chemistry Letters*, vol. 2, No. 4, pp. 295–298, 1992.

"Application of the Vicinal Oxyamination Reaction with Asymmetric Induction to the Hemisynthesis of Taxol and Analogues", L. Mangatal et al, *Tetrahedron*, vol. 45, No. 13, pp. 4177 to 4190, 1989.

"Synthesis of Biologically Active Taxol Analogues with Modified Phenylisoserine Side Chains", Georg et al., *J. Med. Chem.*, 1992, vol. 35, pp. 4230–4237.

*Primary Examiner*—Ba K. Trinh
*Attorney, Agent, or Firm*—Timothy J. Martin

[57] ABSTRACT

A method for producing paclitaxel is accomplished by first esterifying C-7-CBZ baccatin III with a C3'-N-CBZ-C2'-O-protected (2R, 3S)-3-phenylisoserine side chain to form a first intermediate. Next, the carbobenzyloxy groups at C-7 and at the C3' nitrogen site of the first intermediate are respectively replaced with hydrogen and PhCO to produce a second intermediate that is next deprotected at C2' by replacing the protecting group with hydrogen. The C2' protecting group is a benzyl-type protecting group, preferably benzyloxymethyl or benzyl. Excess amounts, such as six equivalents, of the side chain are preferably employed. DMAP and a dialkylcarbodiimide are also preferably used during esterification. Various preferred reaction temperatures, times, and purification steps are disclosed.

15 Claims, No Drawings

METHOD FOR PACLITAXEL SYNTHESIS

FIELD OF THE INVENTION

The present invention is directed to the production of the anti-neoplastic compound paclitaxel. More particularly, it is directed to the production of paclitaxel by esterifying C7-CBZ baccatin III with C3'N-CBZ-C2'-O-protected (2R, 3S)-3-phenylisoserine side chain to produce an intermediate that may thereafter be deprotected to produce paclitaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

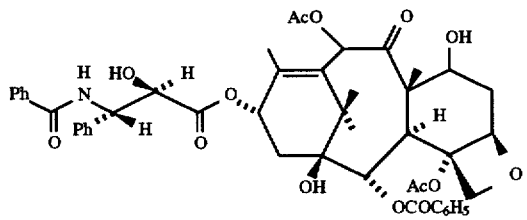

Paclitaxel is a naturally occurring taxane diterpenoid which is found in several species of the yew (genus Taxus, family Taxaceae). Unfortunately, the concentration of this compound is very low. The species of evergreen are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation are discouraging.

While the presence of paclitaxel in the yew tree is in extremely low concentrations, there are a variety of other taxane compounds, such as Baccatin III, cephalomanine, 10-deacetylbaccatin III, etc., which are also able to be extracted from the yew bark. Some of these other taxane compounds are more readily extracted in higher yields. Indeed, a relatively high concentration of 10-deacetylbaccatin III can be extracted from the leaves of the yew as a renewable resource.

In order to successfully synthesize paclitaxel, convenient access to a chiral, non-racemic side chain and an abundant natural source of a usable baccatin III backbone as well as an effective means of joining the two are necessary. However, the esterification of the side chain to the protected baccatin III backbone is difficult because of the sterically hindered C13 hydroxyl in the baccatin III backbone which is located within the concave region of the hemispherical protected baccatin III skeleton.

One technique for the semi-synthesis of paclitaxel is found in co-pending patent application Ser. No. 08/483,081. In this application paclitaxel is synthesized by joining C7-TES baccatin III with N-carbamate protected C2' hydroxyl benzyl-type protected (2R,3S)-3-phenylisoserine, where the C2' hydroxyl is protected by a hydrogenable benzyl-type group such as benzyloxymethyl (BOM) or benzyl. Following the esterification of the protected baccatin III and the protected side chain, the compound may be suitably deprotected, acylated, and further deprotected to yield paclitaxel.

While the existing techniques for synthesizing paclitaxel certainly have merit, there is still a need for improved chemical processes which can produce this anti-cancer compound. The present invention is directed to the synthesis of C7-CBZ protected baccatin III, which can then be esterified with a suitably protected side chain, then the resulting compound deprotected to yield paclitaxel.

SUMMARY OF THE INVENTION

It is an object of the present invention to provide a new and useful method for synthesizing paclitaxel.

It is another object of the present invention to provide a method wherein paclitaxel may be produced by esterifying a protected baccatin III backbone with a suitably protected 3-phenylisoserine side chain that may thereafter be deprotected.

A further object of the present invention is to produce paclitaxel from the esterification of C7-CBZ baccatin III with C3' N-CBZ-C2'-O-protected (2R,3S)-3-phenylisoserine.

Yet another object of the present invention is to produce a useful intermediate in the form of C3' N-CBZ protected C2'-OBOM protected (2R,3S)-3-phenylisoserine C7-CBZ baccatin III which may then be deprotected, acylated and further deprotected to yield paclitaxel.

It is yet another object of the present invention to provide methods for producing paclitaxel which are simplified and which may be suitable for large scale production of paclitaxel for anti-neoplastic applications.

According to the present invention, then, paclitaxel may be produced by esterifying C7-CBZ baccatin III of the formula:

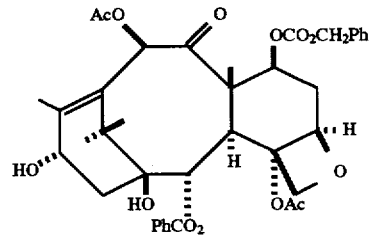

with C3' N-CBZ-C2'-O-protected (2R,3S)-3-phenylisoserine side chain of the formula:

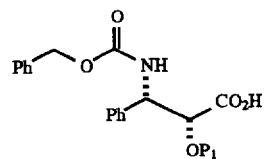

to form a first intermediate compound having the formula:

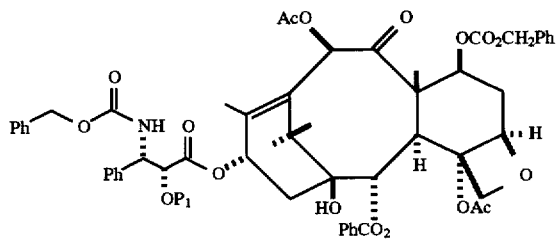

where $P_1$ is a hydrogenable benzyl-type protecting group. Next, the C7 carbobenzyloxy group at C7 is replaced with hydrogen and the carbobenzyloxy group at the C3' nitrogen site is replaced with PhCO to produce a second intermediate compound of the formula:

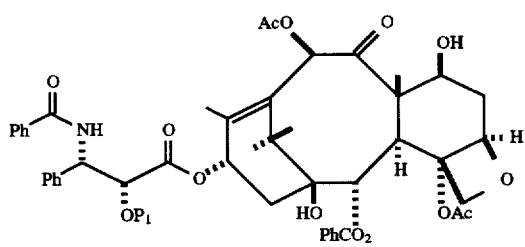

wherein $P_1$ is the hydrogenable benzyl-type protecting group. Finally, the second intermediate compound is deprotected by replacing $P_1$ with hydrogen to produce paclitaxel.

Preferably, the hydrogenable benzyl-type protecting group, $P_1$, is selected from a group consisting of benzyloxymethyl (BOM) and benzyl with BOM being a particularly desirable C2' protecting group. The invention describes a process for producing the C3' N-CBZ-C2' benzyl-type 0-protected (2R,3S)-3-phenylisoserine side chain.

Similarly, the invention describes a method for producing C7 CBZ protected baccatin III, either from baccatin III, itself, or directly from 10-deacetylbaccatin III. In either event, the protected baccatin III backbone is selectively protected at the C7 position.

During the esterification step, it is desired that six (6) equivalents of the N-CBZ C2' protected 3-phenylisoserine side chain is used for each equivalent of the C7-CBZ baccatin III. In the esterification step, also, the side chain of the protected baccatin III compounds are first dissolved in toluene to form a first solution after which dimethylaminopyridine (DMAP) and a dialkylcarbodiimide is added to produce a second solution that contains the first intermediate compound. The dialkylcarbodiimide is preferably mixed in equal proportion to the C3' N-CBZ C2'-O-protected (2R,3S) -3-phenylisoserine, and the dialkylcarbodiimide may be selected from a group consisting of dicyclohexylcarbodiimide and diisopropylcarbodiimide. The esterifying step is also conducted at a temperature that is preferably 60° to 80° C. for a first interval of time.

The first intermediate compound may be purified prior to replacing the C7 and N-C3' carbobenzyloxy groups to form the second intermediate compound, for example, by column chromatography. In any event, the carbobenzyloxy groups at C7 and N-C3' are removed by dissolving the first intermediate compound in isopropanol in the presence of Pearlman's catalyst to form a first mixture. This first mixture is hydrogenated for at least twenty-four hours and concentrated to residue. The residue is then taken up in toluene after which anhydrous potassium carbonate is added, followed by the addition of benzoyl chloride. Finally, the second intermediate compound is deprotected by dissolving the second intermediate compound in isopropanol in a presence of Pearlman's catalyst to form a second mixture. This second mixture is then hydrogenated for at least twenty-four hours.

These and other objects of the present invention will become more readily appreciated and understood from a consideration of the following detailed description of the exemplary embodiment.

DETAILED DESCRIPTION OF THE INVENTION

The present disclosure is broadly directed to a chemical process for the efficient production of paclitaxel as well as intermediate and precursors therefor. More specifically, the present invention discloses a new chemical compound in the form of C7-CBZ baccatin III as a useful intermediate in the production of paclitaxel. The C7-CBZ baccatin III is esterified with an N-CBZ-3-phenylisoserine acid having a hydrogenable benzyl-type hydroxyl protecting group at C2' to join the side chain at the C13 hydroxyl of the protected baccatin III backbone. The general process described herein involves the production of the C7-CBZ baccatin III backbone, the production of the suitably protected N-CBZ-3-phenylisoserine acid having the hydrogenable benzyl-type protecting group C2', the condensation of the two compounds, and the subsequent deprotection to yield paclitaxel.

A. Production of C7-CBZ Protected Baccatin III

According to the present invention, two alternative routes are described for producing C7-CBZ protected baccatin III. Preferably, on one hand, baccatin III can be protected at the C7 site to yield C7-CBZ baccatin III. On the other hand, 10-deacetylbaccatin III (10-DAB) can be directly converted to C7-CBZ baccatin III without going through a baccatin III intermediate. This alternative method using 10-DAB has an advantage since 10-DAB is much more naturally abundant, and thus less expensive, than baccatin III; however, this alternative method has a reduced yield.

Route 1

C7-CBZ baccatin III has the formula:

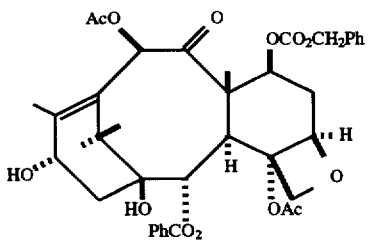

Formula 1 and can be synthesized from baccatin III according to the following reaction:

Reaction I

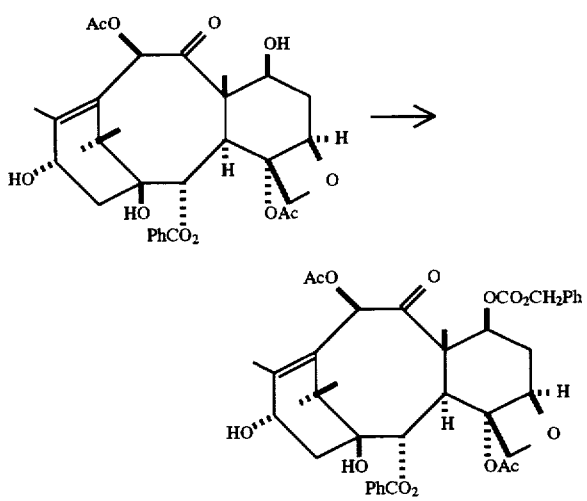

Baccatin III is dissolved in anhydrous THF (tetrahydrofuran) to form a first solution, which is cooled under a nitrogen atmosphere to a reduced temperature of less than −20° C. n-Butyl lithium (1.6 M in hexane) is then added dropwise to the first solution to form a second solution, which is stirred for approximately 5 minutes at the reduced temperature. Benzyl chloroformate (CBZ-Cl) is added dropwise to the second solution to form a third solution which is then stirred and allowed to warm to 0° C. over approximately one (1) hour. The third solution is quenched with cold saturated ammonium chloride to eliminate any excess n-butyl lithium and CBZ-Cl, and the mixture is concentrated under vacuum to yield a first residue. This first residue is next taken up in ethyl acetate and washed once with water to remove unwanted salts. Next, the residue is washed with brine. The organic layer is then dried and concentrated under vacuum to yield a second residue. The second residue is recrystallized or column chromatographed with ethyl acetate:hexane to give C7-CBZ baccatin III as a white solid.

Route 2

Alternatively, C7-CBZ baccatin III can be synthesized directly from 10-deacetyl baccatin III as follows:

Reaction II

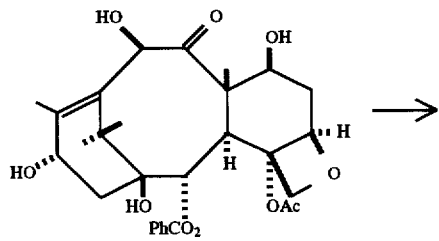

→

-continued
Reaction II

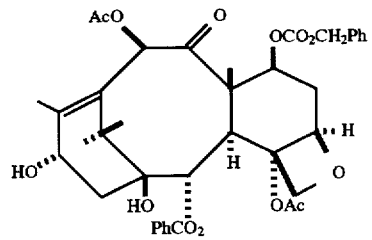

Here, 10-DAB is dissolved in THF to form a first solution which is cooled to a reduced temperature of less than −20° C. under a nitrogen atmosphere. At least 2 equivalents of n-butyl lithium (1.6M in hexane) are then added dropwise to the first solution to form a second solution which is then stirred for approximately 5 minutes at the reduced temperature. Preferably, acetyl chloride (1 equivalent) is added to the second solution to form a third solution which is stirred at the reduced temperature for approximately 30 minutes. Alternatively, acetic anhydride (1 equivalent) may possibly be used in place of the acetyl chloride to acylate the 10-DAB. In either case, benzyl chloroformate (1 equivalent) is next added, and this fourth solution is stirred for an additional thirty (30) minutes at the reduced temperature and then warmed to 0° C. over thirty (30) minutes. The fourth solution is then quenched with cold saturated ammonium chloride at the reduced temperature to remove any excess n-butyl lithium, acetyl chloride and CBZ-Cl; this mixture is then warmed to room temperature. The solvent is removed under vacuum to yield an initial residue which is taken up in ethyl acetate and washed with water to remove unwanted salts. The residue is then washed with brine, dried and concentrated under vacuum to yield a final residue. The final residue is chromatographed (silica gel hexanes:ethyl acetate) to yield C7-CBZ baccatin III. It is important to note that this method represents a direct synthesis of C7-CBZ baccatin III from 10-DAB, as the intermediate formed in this reaction is a C7 lithium alkoxide of baccatin III, that is, the intermediate is not baccatin III itself.

B. Production of the 3-Phenylisoserine Side Chain

The production of the C3' N-CBZ C2' benzyl-type protected (2R,3S)-3-phenylisoserine side chain has been previously disclosed in the co-pending patent application Ser. No. 08/609,083 entitled "Intermediate for Docetaxel Synthesis and Production Method Therefor". This compound has the general formula:

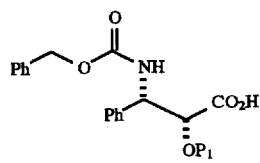

Formula 2

Here, the protecting group on the C2' hydroxyl is a hydrogenable protecting group such as benzyloxymethyl (BOM) or benzyl.

This C3' N-CBZ C2' O-protected (2R,3S)-3-phenylisoserine side chain can be produced according to the following two reactions. The first reaction

Reaction III

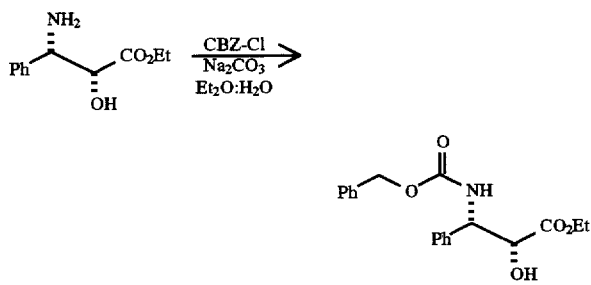

Here, (2R,3S) 3-phenylisoserine ethyl ester is alternatively dissolved in either equal parts diethyl ether:water or equal parts methyl t-butyl ether:water and the solution cooled to 0° C. The sodium carbonate is then added to the solution and benzyl chloroformate is added dropwise over an interval of about five minutes and the resulting mixture stirred at 0° C. for approximately one hour. After the one hour stirring, the solution is poured into water and extracted with methylene chloride or ethyl acetate, as desired. The organic layer is separated, dried and concentrated under vacuum to residue. The residue is then recrystallized from ethyl acetate:hexane to result in C3' N-CBZ (2R,3S)-3-phenylisoserine ethyl ester.

This intermediate was next protected by the hydrogenatable benzyl-type protecting group in several ways. For example, one route to the desired hydrogenatable benzyl-type protected side chain is as follows:

Reaction IV

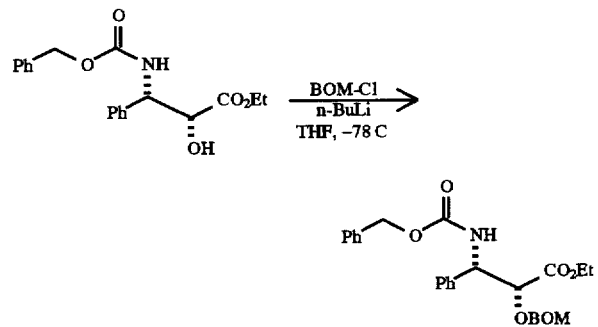

Here, the hydrogenable benzyl-type protecting group is benzyloxymethyl (BOM). To prepare this compound, the C3' N-CBZ (2R,3S)-3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkyllithium agent such as n-butyl lithium, although it is desirable that the alkyllithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes, and the mixture stirred for approximately two to five hours at the reduced temperature. Thereafter, the solution is warmed to 0° C. and quenched with water to eliminate excess n-butyl lithium. The resulting mixture is concentrated under vacuum to residue, and this residue is thereafter taken up in ethyl acetate and washed with water and brine to remove unwanted salts. The organic layer may then be dried and concentrated under vacuum and the residue recrystallized from ethyl acetate:hexane or chromatographed with ethyl acetate:hexane to give the C3' N-CBZ C2'-OBOM (2R,3S)-3-phenylisoserine ethyl ester.

Another route to production of C3' N-CBZ C2'-OBOM (2R,3S)-3-phenylisoserine ethyl ester is accomplished by dissolving the C3' N-CBZ (2R,3S)-3-phenylisoserine ethyl ester in anhydrous methylene chloride. Thereafter, a tertiary amine base such as diisopropylethylamine is added along with BOM-Cl and the mix is refluxed for twenty-four hours. While this reaction route will produce C3' N-CBZ C2'-OBOM (2R,3S)-3-phenylisoserine ethyl ester, the reaction proceeds much slower than the route discussed above, however, it may be preferred because of higher yield. Here, the compound is not purified, but rather is carried on to subsequent processing steps in crude form.

In either instance, the resulting C3' N-CBZ C2'-OBOM (2R,3S)-3-phenylisoserine ethyl ester, either the purified form of the first route or in the crude form from the second route, may simply be converted to the corresponding acid by the reaction:

Reaction V

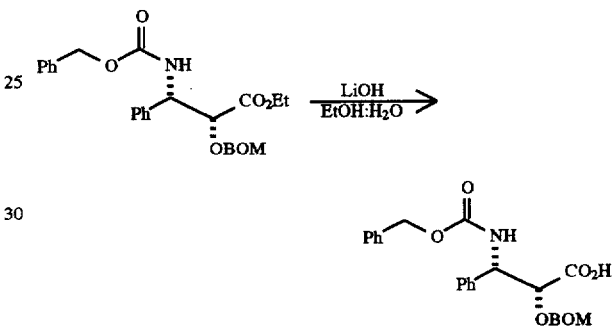

Here, the protected ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N hydrochloric acid) and extracted with ethyl acetate. The resulting organic layer is separated, dried and concentrated under vacuum. The residue acid is then isolated for use without further purification. This produces the desired C3' N-CBZ C2'-OBOM (2R,3S)-3-phenylisoserine.

Where the C3' N-CBZ C2'-OBOM (2R,3S)-3-phenylisoserine ethyl ester is carried forward in the crude form and is converted into C3' N-CBZ-C2'-OBOM (2R,3S)-3-phenylisoserine, it is necessary for further purification of the end product. This purification is accomplished by dissolving the product in toluene followed by the dropwise addition of one equivalent dicyclohexylamine and the resulting solution is stirred for one-half hour. This mixture is then concentrated in vacuo, and the resulting residue is recrystallized from ethyl acetate:hexane to give the dicyclohexylamine salt of the C3' N-CBZ C2'-OBOM (2R,3S)-3-phenylisoserine. The purified C3' N-CBZ C2'-OBOM (2R, 3S)-3-phenylisoserine may then be liberated by dissolving this dicyclohexylamine salt in methylene chloride or other halogenated solvent followed by washing the methylene chloride with several portions of 1N HCl. The organic layer is then washed with several portions of water to remove dicyclohexylamine hydrochloride. Next, it is washed with one portion of saturated brine and reduced in vacuo to give the desired acid.

Benzyl itself is another example of a hydrogenable benzyl-type protecting group that may be used instead of BOM. C3' N-CBZ 2'-benzyl (2R,3S)-3-phenylisoserine ethyl ester was produced as above with the substitution of benzyl bromide for BOM-Cl according to the reaction:

Reaction VI

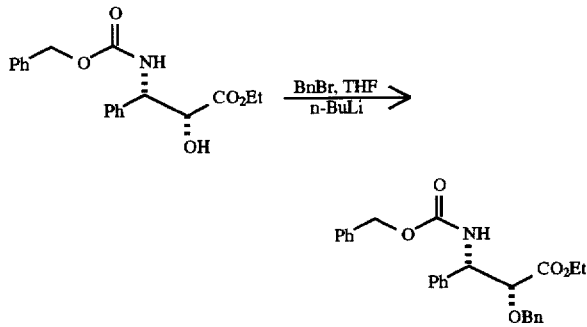

Here, the CBZ protected (2R,3S)-3-phenylisoserine ethyl ester is dissolved in anhydrous THF under a nitrogen atmosphere and cooled to a reduced temperature such as −40° C. or −78°°C. for example in a dry ice/acetone bath followed by the dropwise addition of an alkyllithium agent such as n-butyl lithium, although it is desirable that the alkyllithium agent be a straight chain alkyl. The resulting mixture is stirred for about ten minutes. Benzyl bromide (BnBr) is then added dropwise over an interval of about five minutes and the mixture stirred for approximately two to five hours at the reduced temperature. Thereafter, the solution is warmed to 0° C. and quenched with water to destroy excess n-butyl lithium. The resulting mixture is concentrated under vacuum to residue, and this residue is thereafter taken up in ethyl acetate and washed with water to remove any lithium bromide salt; it is then further washed with brine. The organic layer may then be dried and concentrated under vacuum and the residue recrystallized from ethyl acetate-:hexane or chromatographed with ethyl acetate:hexane to give C3' N-CBZ 2'-benzyl (2R,3S)-3-phenylisoserine ethyl ester.

Alternatively, the C3' N-CBZ C2'-benzyl (2R,3S)-3-phenylisoserine ethyl ester may be obtained according to the reaction:

Reaction VII

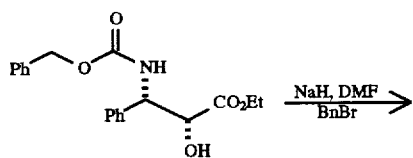

-continued
Reaction VII

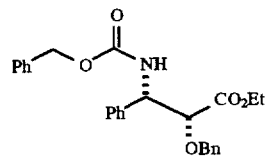

Here, to a stirred solution of NaH in anhydrous DMF under nitrogen is added C3' N-CBZ (2R,3S)-3-phenylisoserine ethyl ester dissolved in DMF over five minutes. The mixture is then stirred at 0° C. for one half hour. Then benzyl bromide (1.1 equivalents) is added dropwise over five minutes and the reaction is stirred for two hours. The mixture is then quenched with water to destroy excess sodium hydride. Thereafter, either diethyl ether or methyl t-butyl ether is added. The organic layer is then washed with four portions of water to remove DMF and sodium bromide. Next, it is washed with brine and then dried and concentrated under vacuum to produce C3' N-CBZ C2'-benzyl (2R,3S)-3-phenylisoserine ethyl ester may then be readily converted into N-CBZ C2'-benzyl 3-phenylisoserine by the process of Reaction IV above with the understanding that, in this case, benzyl is the C2' protecting group instead of benzyloxymethyl (BOM).

C. Esterification of C7-CBZ Baccatin III and the Side Chain

Esterification of C7-CBZ baccatin III with the C3' N-CBZ C2'-protected (2R,3S)-3-phenylisoserine side chain (where the C2' hydroxyl is protected by any hydrogenable protecting group) may be accomplished as follows. The preferred hydrogenable benzyl group shown below is BOM (benzyloxymethyl).

Reaction VIII

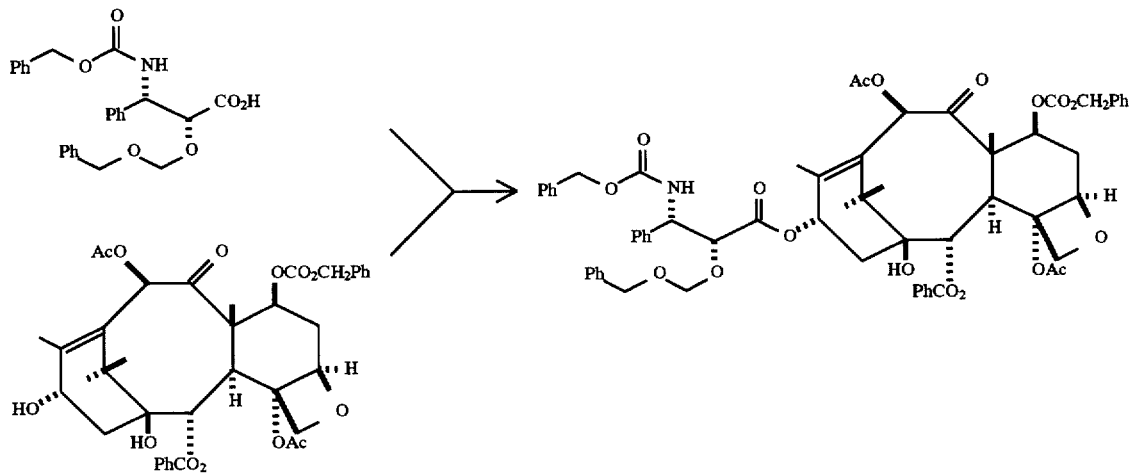

Here the C7-CBZ baccatin III (1 equivalent) and the acid side chain (6 equivalents) are dissolved in toluene. To this mixture, 0.5 equivalents of DMAP (dimethylamino pyridine) and preferably 6 equivalents of dicyclohexylcarbodiimide (DCC) are added, and the resulting mixture heated at 70° C. for thirty (30) minutes to one (1) hour although the range of temperature could be 60° C. to 80° C. It should also be noted however that noted however that other dialkyl carbodiimides may be substituted for the DCC, with one example being diisopropylcarbodiimide.

Next, the solution is cooled to room temperature and an equal volume of ethyl acetate or diethyl ether is added to the solution. The resulting mixture is then cooled to 0° C. and held at this temperature for twenty-four (24) hours. After this time it is filtered, and the residue is rinsed with either diethyl ether or ethyl acetate. The combined organics are then washed with hydrochloric acid (5%), water, and finally brine. The organic phase is separated, dried and concentrated under vacuum. The resulting residue is then dissolved in ethyl acetate:hexane and eluted over a silica gel plug. The eluent is then concentrated under vacuum to result in the esterified compound:

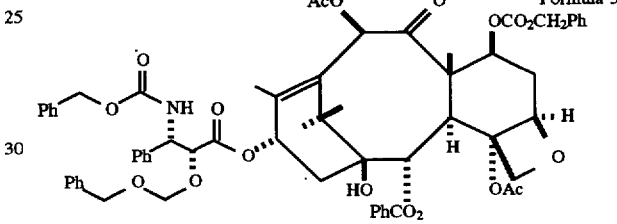

Formula 3

D. Deprotection to Paclitaxel

The compound according to formula 3 may now be converted into paclitaxel by removing the nitrogen and C7 CBZ groups, putting the benzoyl group onto the nitrogen, and finally removing the C2' benzyl-type protecting group. Removal of the CBZ groups, and subsequent addition of the benzoyl group to the nitrogen are accomplished as follows (BOM is shown as the protecting group at the C2' hydroxyl site, although benzyl could also be used):

Reaction IX

Here, the coupled product of formula 3 is dissolved in isopropanol to which the Pearlman's catalyst is added. The resulting mixture is hydrogenated at 40 psi for twenty-four hours, although alternatively, the mixture can be stirred under one atmosphere of hydrogen for 24 hours. Thereafter, the mixture is filtered through diatomaceous earth and reduced under vacuum to residue. Preferably, the residue is taken up in toluene and anhydrous potassium carbonate added. Alternatively, the residue may be taken up in ethyl acetate or toluene and a tertiary amine base, such as triethylamine, is added. In either case, benzoyl chloride is then added dropwise, and the mixture stirred for two hours. The resulting mixture is then washed with water and finally brine. The resulting organic phase is then separated, dried, and concentrated under vacuum to yield C2'-BOM paclitaxel.

Finally, the C2'-BOM is removed according to the following reaction:

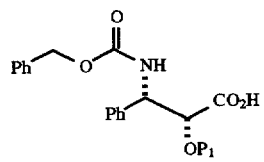

Reaction X

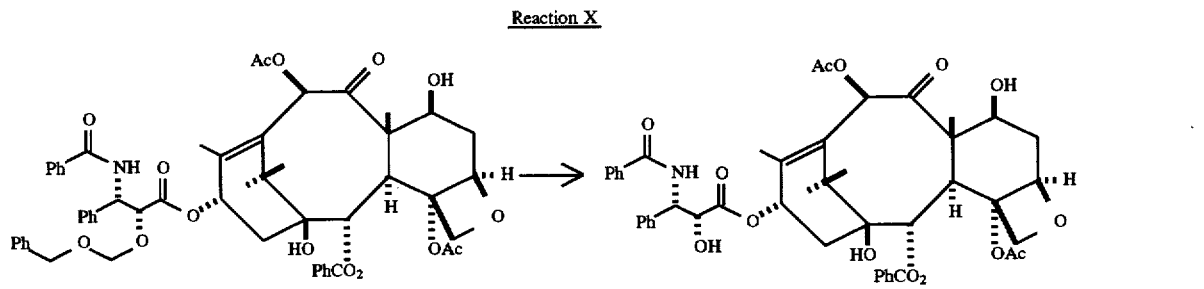

The BOM protected paclitaxel is dissolved in isopropanol to which Pearlman's catalyst is added. This mixture is hydrogenated for 24 hours under 40 psi hydrogen to yield paclitaxel.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A method of producing paclitaxel, comprising the steps of:

(a) esterifying C7-CBZ baccatin III of the formula:

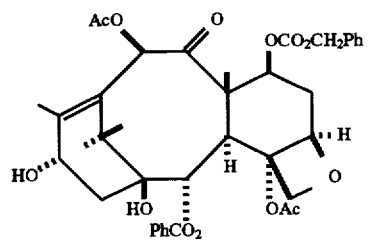

with C3' N-CBZ-C2'-O-protected (2R,3S)-3-phenylisoserine side chain of the formula:

to form a first intermediate compound of the formula:

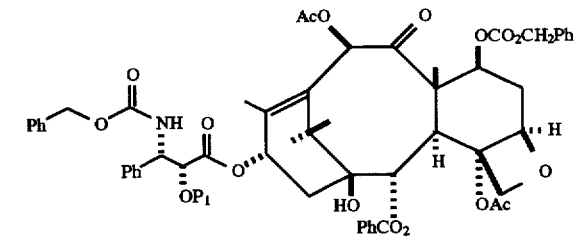

wherein $P_1$ is a hydrogenable benzyl-type protecting group;

(b) replacing the C7 carbobenzyloxy group with hydrogen and replacing the carbobenzyloxy group at the C3' nitrogen site with PhCO to produce a second intermediate compound of the formula:

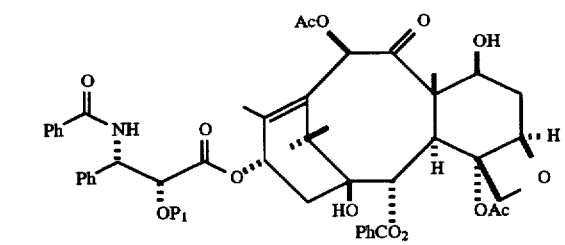

wherein $P_1$ is the hydrogenable benzyl-type protecting group and (c) deprotecting the second intermediate compound by replacing $P_1$ with hydrogen to produce paclitaxel.

2. The method of producing paclitaxel according to claim 1 wherein $P_1$ is selected from a group consisting of benzyloxymethyl and benzyl.

3. The method of producing paclitaxel according to claim 1 wherein six equivalents of the C3' N-CBZ C2'-O-protected (2R,3S)-3-phenylisoserine side chain is used for each equivalent of the C7-CBZ baccatin III during the esterifying step.

4. The method of producing paclitaxel according to claim 1 wherein the C3' N-CBZ C2'-O-protected (2R,3S)-3-phenylisoserine side chain and the C7-CBZ baccatin III are dissolved in toluene to form a first solution during the esterifying step after which DMAP and a dialkylcarbodiimide is added to the first solution to produce a second solution containing the first intermediate compound.

5. The method of producing paclitaxel according to claim 4 wherein the dialkylcarbodiimide is in equal proportion to the C3' N-CBZ C2'-O-protected (2R,3S)-3-phenylisoserine.

6. The method of producing paclitaxel according to claim 4 wherein the dialkylcarbodiimide is selected from a group consisting of dicyclohexylcarbodiimnide and diisopropylcarbodiimide.

7. The method of producing paclitaxel according to claim 4 wherein the esterifying step is conducted at a first temperature of 60°–80° for a first interval.

8. The method of producing paclitaxel according to claim 1 wherein the esterifying step is conducted at a first temperature of 60°–80° for a first interval.

9. The method of producing paclitaxel according to claim 1 wherein the first intermediate compound is dissolved in a solution and is column chromatographed to purify the first intermediate compound prior to replacing the C7 and N-C3' carbobenzyloxy groups to form the second intermediate compound.

10. The method of producing paclitaxel according to claim 1 wherein the step of replacing the carbobenzyloxy groups is accomplished by dissolving the first intermediate compound in isopropanol in the presence of Pearlman's catalyst to form a first mixture.

11. The method of producing paclitaxel according to claim 10 wherein the first mixture is hydrogenated for at least twenty-four hours.

12. The method of producing paclitaxel according to claim 11 wherein the first mixture is concentrated to residue after being hydrogenated.

13. The method of producing paclitaxel according to claim 12 wherein said residue is taken up in toluene after which anhydrous potassium carbonate is added followed by an addition of benzoyl chloride.

14. The method of producing paclitaxel according to claim 1 wherein the step of deprotecting the second intermediate compound is accomplished by dissolving the second intermediate compound in isopropanol in a presence of Pearlman's catalyst to form a second mixture.

15. The method of producing paclitaxel according to claim 14 wherein the second mixture is hydrogenated at elevated pressure for at least twenty-four hours.

* * * * *